United States Patent [19]
Watanabe et al.

[11] Patent Number: 4,851,342
[45] Date of Patent: Jul. 25, 1989

[54] METHOD FOR PRODUCING ACRYLAMIDE USING A MICROORGANISM

[75] Inventors: Ichiro Watanabe; Yasuo Ogawa; Susumu Seki, all of Kanagawa, Japan

[73] Assignees: Nitto Chemical Industry Co., Ltd.; Mitsubishi Rayon Co., Ltd., both of Tokyo, Japan

[21] Appl. No.: 692,758

[22] Filed: Jan. 18, 1985

[30] Foreign Application Priority Data

Jan. 20, 1984 [JP] Japan .................................. 59-7290

[51] Int. Cl.$^4$ ...................... C12P 13/02; C12N 9/80; C12R 1/15; C12R 1/365
[52] U.S. Cl. .................................... 435/129; 435/228; 435/843; 435/872
[58] Field of Search ............... 435/128, 253, 129, 228, 435/843, 872

[56] References Cited

U.S. PATENT DOCUMENTS 4,248,968  2/1981  Watanabe et al. ................. 435/129

*Primary Examiner*—Elizabeth C. Weimar
*Attorney, Agent, or Firm*—Sughrue, Mion, Zinn, Macpeak & Seas

[57] ABSTRACT

A method is described for producing acrylamide from acrylonitrile by the action of a microorganism having nitrilase activity in an aqueous medium, which comprises conducting the reaction in the presence of an alkali metal sulfate at an ionic activity of from 0.004 to 0.01 mole per liter while controlling the pH of said aqueous medium within a range of from 7 to 9 with an alkali hydroxide.

9 Claims, No Drawings

METHOD FOR PRODUCING ACRYLAMIDE USING A MICROORGANISM

FIELD OF THE INVENTION

This invention relates to a microbial method for producing aqueous acrylamide solutions of very high quality.

BACKGROUND OF THE INVENTION

It is known that some microorganisms having nitrilase activity have the ability to convert acrylonitrile to acrylamide through hydration. Such microorganisms so far known include microorganisms belonging to the genera Bacillus, Bacteridium, Micrococcus and Brevibacterium (e.g.,see U.S. Pat. No. 4,001,081, British Pat. No. 1,535,307, German OLS (laid open) No. 2,556,701, and French Pat. No. 2,294,999) the genera Corynebacterium and Nocardia (e.g., see U.S. Pat. No. 4,248,968, British Pat. No. 2,018,240, German OLS (laid open) No. 2,921,292, and French Pat. No. 2,421,212) and the genus Pseudomonas (e.g., see European Pat. No. 93.782).

In producing acrylamide from acrylonitrile using such microorganisms, acrylonitrile is subjected to catalyiic reaction in an aqueous medium (e.g. water, physiological saline, phosphate buffer) using the microbial cells either as is or immobilized, for instance, with a polymer gel. For smooth progress of the enzymatic reaction, the following conditions are generally used: a substrate acrylonitrile concentration of from 0.1 to 10 percent by weight; a cell concentration of from 0.01 to 10 percent by weight; a PH of from 7 to 9; a temperature range of from the freezing point of the aqueous medium to 30° C.; and a time period of from 0.5 to 100 hours.

Currently, semibatchwise or continuous processes using granular immobilized cells are preferred from the viewpoints of prevention of impurity migration from the cells, separability of the cells from reaction mixtures, reusability of the cells, increased enzyme stability, etc., and thus are widely used in carrying out microbial reactions. Such processes are also economically advantageous in the microbial production of acrylamide, and the present inventors have already provided a method for producing acrylamide by continuous column reaction using immobilized cells entrapped with a polyacrylamide gel, for instance (e.g., see Japanese Patent Publication No. 1234/82 and U.S. Pat. No. 4,248,968).

However, irrespective of whether the cells are used as is or in the immobilized state, the use of the above-mentioned physiological saline, phosphate buffer, or the like as the aqueous medium is not preferable from the viewpoint of quality, since use thereof means that the product, i.e., the aqueous acrylamide solution, will contain sodium chloride, phosphates, etc., in large amounts. In particular, the presence of phosphates may result in unfavorable results, for example in that, in producing acrylamide polymers having a high degree of polymerization, the polymers obtained are often more or less insoluble in water. Therefore, in such a case, some aftertreatment for removing the salts, such as an ion exchange treatment, becomes essential. This makes the operational procedure complicated and troublesome, and hence is unfavorable from an economic viewpoint.

On the other hand, the use of water alone as the aqueous medium also presents problems. For instance, when the reaction is carried out in a water system without using physiological saline or phosphate buffer, the enzyme activity of the cells is apt to fall rapidly. Moreover, when the hydration reaction is carried out continuously using a column packed, for instance, with polyacrylamide gel-immobilized cells, the immobilized cells in said column becomes swollen in a short period of time after the start of the reaction, whereby smooth operation of the procsss becomes impossible.

Thus, in the microbial production of acrylamide, contradictory problems are encountered. When much importance is attached to economic efficiency, and hence stabilization of the cellular enzymes is aimed at, a large amount of salts must be present in the reaction mixture; accordingly, the purity of the product, i.e., the aqueous acrylamide solution, is decreased. When, on the other hand, the purity (quality) of the aqueous acrylamide solution is regarded as more important, the stability of the cellular enzymes tend to be decreased under the conditions that have been used, so that the cost of cell preparation accounts for a great part of the cost of acrylamide production, which is economically disadvantageous.

To overcome such problems, the present inventors previously conducted investigations to try to find a method which might allow the desired reactions to proceed under those conditions employable in producing high-purity aqueous acrylamide solutions, while simultaneously retaining the stability of cellular enzymes for a long period of time. As a result, there was proposed (1) a method which comprises carrying out the reaction in an aqueous medium containing a small amount of an alkali metal carbonate or bicarbonate as an additive incapable of adversely affecting the polymerizability of the product acrylamide, and also, under some conditions, an organic carboxylic acid (e.g., see U.S. Pat. No. 4,343,900, British Patent Specification No. 2,062,625, German OLS (laid open) No. 3,037,009, French Pat. No. 2,466,506); and (2) a method which allows the reaction to proceed in a salt-free aqueous medium while maintaining cellular enzymes in a stable state, which comprises using immobilized cells entrapped with a cationic acrylamide polymer gel (e.g., see U.S. Pat. No. 4,421,855, British Patent Specification No. 2,086,376, German OLS (laid open) No. 3,132,493, French Patent Application (laid open) No. 2,488,908).

However, the salt concentration in the former method (1) is about 0.1 wt. %, as seen in the examples of the references in the former (1). This concentration was selected while giving priority to the matter of the swelling of immobilized cells in columns for continuous reaction, and therefore it is still a relatively high salt concentration, although the salt selected does not particularly adversely affect the quality of the product, i.e., the aqueous acrylamide solution. The combined use of an organic acid such as acrylic acid is also undesirable when high-purity aqueous acrylamide solutions are required, since the addition of such acid constitutes the addition of a byproduct of the reaction. Therefore, if aqueous acrylamide solutions of higher quality (purity) are desired, it is necessary to search for a compound effective even in lower concentrations.

The latter method (2) was proposed as a method allowing the reaction to proceed in the substantial absence of any salt while maintaining cellular enzymes in a stable state. In method (2), the cellular enzyme has improved stability in the salt-free reaction system as compared, for instance, with previously known polyacrylamide-immobilized cells. However, it is undeniable that the cellular enzyme stability to endure the reaction over a prolonged period of time in method (2) is somewhat inferior as compared with phosphate buffer reaction systems.

SUMMARY OF THE INVENTION

Accordingly, in search for an aqueous medium comparable in cellular enzyme stability to ordinary phosphate buffers, the present inventors conducted extensive studies, from the viewpoints of production of very high quality (purity) aqueous acrylamide solutions, the kinds and amounts of salt that could be added to the aqueous reaction system to achieve the desired result. As a result, it has been found that the stability cellular enzyme largely depends on the ionic activity rather than the concentration of a salt and that even when the ionic activity of an aqueous reaction solution is reduced to 0.004 mole/liter, the cellular enzyme stability during reaction is almost the same as in the case of physiological saline used at a concentration of 0.85 wt % or phosphate buffers used at a concentration of from 0.05 to 0.1M. The ionic activity is expressed by the formula $$I = \tfrac{1}{2}\Sigma m_i z_i^2$$

wherein $m_i$ is the molar concentration of the ion and $z_i$ is the valence of the ion. A salt which shows great ionic activity in a small amount is preferred as the salt to be added. Such salt is, for example, a salt of a monovalent cation and a polyvalent (divalent or trivalent) anion, and thus it was thought that the use of such salt might greatly contribute to the stabilization of cellular enzymes even in a relatively low salt concentration in the aqueous medium. Such salts include sulfates, phosphates, and borates of sodium, potassium, ammonium, etc. However attempts to conduct the hydration of acrylonitrile for acrylamide production using these salts in the form of aqueous solutions revealed that the use of ammonium as the cation or of borate as the anion leads to unsatisfactory cellular enzyme stability, and that although the use of phosphate as the anion is favorable from the viewpoint of cellular enzyme stability, the presence of a phosphate, even in such a concentration, leads to deterioration in quality of the product, aqueous acrylamide solution, as mentioned above. In conclusion, it was found that sodium sulfate and potassium sulfate are particularly effective salts for the intended purpose.

The present invention, which has been completed based on the above findings, involves a method using salts which provide a great ionic activity in a small amount and are inert with respect to the polymerizability of the acrylamide.

Thus, the present invention provides a method for producing acrylamide from acrylonitrile by the action of a microorganism having nitrilase activity in an aqueous medium, which comprises conducting the reaction in the presence of an alkali metal sulfate at an ionic activity of from 0.004 to 0.01 mole per liter while controlling the pH of said aqueous medium within a range of from 7 to 9 with an alkali hydroxide.

DETAILED DESCRIPTION OF THE INVENTION

Any microorganism having the ability to hydrolyze acrylonitrile and form acrylamide may be used as the microorganism for carrying out the invention, regardless of the taxonomic position thereof. Thus, the strain N-771 belonging to the genus Corynebacterium (deposited at the Fermentation Research Institute, Agency of Industrial Science and Technology, Ministry of International Trade and Industry, Japan, as FERM-P No. 4445), the strain N-774 belonging to the genus Corynebacterium (deposited at the Fermentation Research Institute, Agency of Industrial Science and Technology, Ministry of International Trade and Industry, Japan, as FERM-P No. 4446) and the strain N-775 belonging to the genus Nocardia (deposited at the Fermentation Research Institute, Agency of Industrial Science and Technology, Ministry of International Trade and Industry, Japan, as FERM-P No. 4447) may be mentioned as suitable examples. These microorganisms may be used either in the form of cells as is or in the form of immobilized cells. When they are to be used in the immobilized form, the commonly used entrapping method which uses polyacrylamide, collagen, gelatin, carrageenan, agar and other gels may be employed. The entrapping method using polyacrylamide is particularly preferred in view of the fact that acrylamide is to be produced in the practice of the invention.

The immobilized cells by the entrapping method can be prepared by a conventional method as described, for example, in U.S. Pat. No. 4,248,968. For preparing polyacrylamide gel-immobilized cells, for instance, monomeric acrylamide and N,N'-methylenebisacrylamide are mixed with a suspension of glutaraldehyde-treated cells, then potassium persulfate and dimethyl-aminopropionitrile, which constitut a catalyst system, are added, and the mixture is maintained at a pH of from 6.5 to 8.5 and a temperature of 0° C. to 10° C. for 30 to 60 minutes to thereby effect polymerization. There is thus obtained a cell-embracing lumpy gel, i.e., immobilized cells entrapped with a polyacrylamide gel.

The alkali metal sulfates to be present in the aqueous medium in accordance with the invention include sodium sulfate and potassium sulfate, among others. The amount of the sulfate is such that the acrylonitrile-containing aqueous medium has an ionic activity of from 0.004 to 0.01 mole/liter, which corresponds to a salt concentration as small as 0.0189 to 0.0473 percent by weight on the reaction mixture basis.

Furthermore, since the above-mentioned salts are all neutral salts and are inert with respect to polymerization of the acrylamide, their presence in such small amounts in product aqueous acrylamide solutions does not exert any substantial influence on the polymerizability of acrylamide.

The following is a typical mode of practice of the present invention.

In practicing the invention, one or more of the above-mentioned microorganisms, for instance, are selected, cells thereof, either as is or in the form of granules of polyacrylamide gel-immobilized cells having an appropriate grain size, are suspended in an aqueous medium having an ionic activity of from 0.004 to 0.01 mole/liter as produced using sodium sulfate. To the suspension, acrylonitrile is added dropwise with stirring. To maintain cellular enzymes in a more stable state, the pH of the reaction system is controlled so as to fall within a range of from 7 to 9, and preferably from 7.5 to 8.5; the temperature is preferably maintained at a temperature of from the freezing point of the aqueous medium to 30° C., and more preferably from the freezing point to 15° C.; and the acrylonitrile concentration is preferably maintained within a range of from 0.1 to 10 percent by weight, and more preferably not more than 3 percent by weight. The reaction may be conducted batchwise (inclusive of semibatchwise) or continuously. By adequately selecting the cell concentration and reaction time while keeping the above parameters within the respective specified ranges, colorless and transparent (APHA color number of not more than 10) aqueous acrylamide solutions having a concentration of up to 30 percent by weight can be obtained at a conversion rate of about 100%.

The aqueous acrylamide solutions obtained after removal of cells or immobilized cells from the reaction mixtures by the conventional method contain very small amounts of sodium sulfate, potassium sulfate, etc., but are almost free of impurities possibly affecting the polymerization of acrylamide adversely. Therefore, said aqueous solutions can be used, directly or after concentration by a conventional method, as materials for the manufacture of a variety of polymers for use as macromolecular flocculants or paper reinforcing agents.

The invention is further illustrated by the following examples, wherein the "part(s)" and "%" values are by weight. Analysis for acrylonitrile, acrylamide, acrylic acid, etc., were all performed by gas chromatography.

EXAMPLE 1

A mixture of 4 parts of washed cells (water content 80%) of the strain N-774 prepared by aerobic cultivation in a medium (pH 7.2) comprising 1% glucose, 0.5% peptone, 0.3% yeast extract and 0.3% malt extract, 847 parts of an aqueous sodium sulfate solution having an ionic activity of 0.0075 mole/liter and 9 parts of acrylonitrile was stirred at 0° C. while keeping a pH of 8.5 and an acrylonitrile concentration of 1% by adding 1/20N sodium hydroxide and acrylonitrile, respectively. In this manner, 140 parts of acrylonitrile was added over about 4.5 hours. Thereafter, stirring was continued for further 3 hours to drive the reaction to completion. Removal of cells by centrifugation gave a colorless, transparent liquid. This aqueous solution had an acrylamide concentration of 20%. Unreacted acrylonitrile was scarcely detected.

This aqueous solution was concentrated in a flash evaporator at 45° C. under reduced pressure while blowing air thereinto, giving a 50% aqueous acrylamide solution. This was usable as is as a material for the manufacture of various polymers (e.g., flocculants, stock additives, oil recovery agents, etc.).

EXAMPLE 2

To 50 parts of washed cells of the strain N-774 prepared as described in Example 1, 0.4 parts of 50% aqueous gultaraldehyde solution and 9.6 parts of 0.05M phosphate buffer (pH 8.0) were added, and the mixture was maintained at 10° C. or below for 30 minutes with stirring. This cell suspension was mixed with 9.5 parts of acylamide, 0.5 part of N,N'-methylenebisacrylamide and 15 parts of 0.05M phosphate buffer to prepare a uniform suspension. Thereto were added 5 parts of 5% aqueous dimethylaminopropionitrile solution and 10 parts of 2.5% aqueous potassium persulfate solution. The mixture was maintained at 10° C. or below for 1 hour to thereby effect polymerization and gelation. The thus-obtained cell-containing lumpy gel was broken to small grains, which were washed well with 0.5% aqueous sodium sulfate solution (pH 8.5) to remove impurities. Thus were obtained 100 parts of immobilized cells.

The immobilized cells (8 parts) 830 parts of aqueous sodium sulfate solution having an ionic activity of 0.0075 mole/liter and 25 parts of acrylonitrile were mixed. The mixture was stirred at 0° C. while maintaining a pH of 8.5 and an acrylonitrile concentration of 3% by addition of 1/20N sodium hydroxide and acrylonitrile, respectively. In this way, 162 parts of acrylonitrile was added over about 6 hours. Thereafter, the mixture was further stirred for 20 hours to drive the reaction to completion. The reaction mixture was allowed to stand, whereby a colorless, transparent supernatant and the immobilized cells were separated. The supernatant had an acrylamide concentration of 25%. While acrylic acid was detected in trace amounts, unreacted acrylonitrile was scarcely detected.

This aqueous solution was concentrated in a flash evaporator at 45° C. under reduced pressure to give a 50% aqueous acrylamide solution. This was usable as is as a material for various ploymers as described in Example 1.

EXAMPLES 3-6 and COMPARATIVE EXAMPLES 1-3

Five parts of washed cells of the N-774 strain prepared as described in Example 1, 846 parts of an aqueous sodium sulfate solution differring in ionic activity and 17 parts of acrylonitrile were mixed. The mixture was stirred at 0° C. while maintaining a pH of from 7.5 to 8.0 and an acrylonitrile concentration of from 2 to 1% by addition of acrylonitrile and 1/20N sodium hydroxide, respectively. The reaction was conducte semibatchwise and the acrylamide formation, or accumulation, was followed as a function of time. The acrylamide concentrations (%) after 2, 5, and 8 hours of reaction in aqueous sodium sulfat solution systems differing in ionic activity are shown in Table 1.

For comparison, the same procedure as above was followed using a 0.05M potassium.sodium phosphate buffer (ionic activity: about 0.15 mole/liter) in place of the aqueous sodium sulfate solution, without addition of sodium hydroxide for pH adjustment, since such pH adjustment was unnecessary in this case.

From the results obtanned (Table 1), it is seen that when the ionic activity of the aqueous sodium sulfate solution is lower than 0.004 mole/liter, the acrylamide accumulation is poor as compared with the case where the 0.05M potassium.sodium phosphate buffer is used; hence such low-concentration sodium sulfate solution is not preferable as the reaction medium.

TABLE 1

| Experiment No. | Comparative Example | | | Example | | | |
|---|---|---|---|---|---|---|---|
| | 1 | 2 | 3 | 3 | 4 | 5 | 6 |
| Ionic Activity (mole/liter) | *ca. 0.15 | 0 | 0.002 | 0.004 | 0.0075 | 0.015 | 0.03 |
| Reaction** Time(hour) | | | | | | | |
| 2 | 10.5 | 9.4 | 9.5 | 10.0 | 11.0 | 10.5 | 11.0 |
| 5 | 19.3 | 15.5 | 15.8 | 17.0 | 19.7 | 19.2 | 19.5 |
| 8 | 20.8 | 17.2 | 17.5 | 20.4 | 21.7 | 20.7 | 21.3 |

*0.05 M potassium.sodium phosphate buffer.
**Each value listed under the Examples and Comparative Examples in the reaction time portion of the table is the acrylamide concentration (%).

EXAMPLE 7 and COMPARATIVE EXAMPLE 4

Four parts of immobilized cells of the strain N-774 prepared as described in Example 2 were mixed with 847 parts of aqeeous potassium sulfate solution having an ionic activity of 0.0075 mole/liter and 17 parts of acrylonitrile, and the mixture was stirred at 0° C. while maintaining a pH of 8.5 and an acrylonitrile concentration of 2% by addition of 1/20N potassium hydroxide and acrylonitrile, respectively.

For comparison, the above reaction procedure was followed using a 0.05M potassium phosphate buffer (ionic activity: about 0.15 mole/liter) in place of the aqueous potassium sulfate solution. Adjustment of pH with potassium hydroxide was also unnecessary in this case. In each case, 132 parts of acrylonitrile was added over about 12 hours, followed by further stirring for 18 hours to drive the reaction to completion. The reaction mixture was allowed to stand, and, after separation of the immobilized cells, there was obtained a colorless, transparent supernatant. Both the supernatant liquids obtained in such manner had an acrylamide concentration of 20%. Although trace amounts of acrylic acid were detected, unreacted acrylonitrile could scarcely be detected.

These aqueous solutions were individually concentrated in a flash evaporator at 45° C. while blowing air thereinto, thereby providing 50% aqueous acrylamide solutions. The 50% solutions were used in an attempt to manufacture polymers suited for use as high-molecular-weight polyacrylamide flocculants. Whereas the potassium sulfate-containing concentrate gave a satisfactory polymer, the polymer obtained from the potassium phosphate buffer-containing concentrate was partly insoluble in water and thus failed to give a satisfactory polyacrylamide flocculant.

While the invention has been described in detail and with reference to specific embodiments thereof, it will be apparent to one skilled in the art that various changes and modifications can be made therein without departing from the spirit and scope thereof.

What is claimed is:

1. A method for producing acrylamide from acrylonitrile by the action of a microorganism having nitrilase activity in an aqueous medium, which comprises conducting the reaction in the presence of sodium sulfate or potassium sulfate at an ionic activity of from 0.004 to 0.01 mole per liter while controlling the pH of said aqueous medium with a range of from 7 to 9 with an alkali hydroxide.

2. A method as in claim 1, wherein the pH is controlled within a range of from 7.5 to 8.5.

3. A method as in claim 1, wherein the reaction is carried out at a temperature within a range of from the freezing point of the aqueous medium to 30° C.

4. A method as in claim 3, wherein the reaction is carried out at a temperature within a range of from the freezing point of the aqueous medium to 15° C.

5. A method as in claim 1, wherein the reaction is carried out at an acrylonitrile concentration of from 0.1 to 10 percent by weight.

6. A method as in claim 5, where in the reaction is carried out at an acrylonitrile concentration of from 0.1 to 3% by weight.

7. A method as in claim 1, wherein the microorganism is selected from the group consisting of Corynebacterium N-771 strain, Corynebacterium N-774 strain, and Nocardia N-775 strain.

8. A method as in claim 1, wherein the microorganisms are immobilized with a polymer gel.

9. A method as in claim 8, wherein the immobilized microorganisms are entrapped with a polyacrylamide and related polymer gel.

* * * * *